United States Patent
Nori et al.

(10) Patent No.: US 10,358,391 B2
(45) Date of Patent: Jul. 23, 2019

(54) BIOSTIMULANT FORMULATION FOR IMPROVING PLANT GROWTH AND USES THEREOF

(71) Applicant: SEA6 ENERGY PRIVATE LTD., Karnataka, Bangalore (IN)

(72) Inventors: Sri Sailaja Nori, Bangalore (IN); Sawan Kumar, Bangalore (IN); Sachin Khandelwal, Bangalore (IN); Shrikumar Suryanarayan, Bangalore (IN)

(73) Assignee: SEA6 ENERGY PRIVATE LTD., Bangalore (IN)

( * ) Notice: Subject to any disclaimer, the term of this patent is extended or adjusted under 35 U.S.C. 154(b) by 104 days.

(21) Appl. No.: 15/529,434

(22) PCT Filed: May 9, 2016

(86) PCT No.: PCT/IN2016/050133
§ 371 (c)(1),
(2) Date: May 24, 2017

(87) PCT Pub. No.: WO2016/181411
PCT Pub. Date: Nov. 17, 2016

(65) Prior Publication Data
US 2017/0334794 A1  Nov. 23, 2017

(30) Foreign Application Priority Data
May 10, 2015  (IN) ............................ 2364/CHE/2015

(51) Int. Cl.
*C05F 11/00* (2006.01)
*C05G 3/00* (2006.01)
(Continued)

(52) U.S. Cl.
CPC .............. *C05B 17/00* (2013.01); *A01N 65/03* (2013.01); *C05F 11/00* (2013.01); *C05G 3/0076* (2013.01); *C08B 37/0003* (2013.01); *C08L 5/00* (2013.01)

(58) Field of Classification Search
None
See application file for complete search history.

(56) References Cited

U.S. PATENT DOCUMENTS

| | | | |
|---|---|---|---|
| 6,893,479 B2 | 5/2005 | Eswaran et al. | |
| 2004/0031302 A1* | 2/2004 | Eswaran | C05F 11/00 71/23 |

(Continued)

FOREIGN PATENT DOCUMENTS

| | | | |
|---|---|---|---|
| WO | WO 2016/181411 A1 | | 11/1916 |
| WO | WO 93/06730 | * | 4/1993 |
| WO | WO 2011/027360 A1 | | 3/2011 |

OTHER PUBLICATIONS

International Search Report and Written Opinion received in PCT Application No. PCT/IN2016/050133 dated Oct. 10, 2016.

*Primary Examiner* — Wayne A Langel
(74) *Attorney, Agent, or Firm* — Brinks Gilson & Lione

(57) ABSTRACT

A biostimulant formulation for promoting plant growth, comprising: juice obtained from at least one seaweed species; and hydrolysate obtained from at least one seaweed species pulp, wherein the hydrolysate is obtained from the pulp after juice has been extracted. A method of preparing the biostimulant formulation. A method of contacting the biostimulant formulation with plant to promote the plant growth.

18 Claims, 3 Drawing Sheets

(51) Int. Cl.
    *C05B 17/00*     (2006.01)
    *A01N 65/03*     (2009.01)
    *C08B 37/00*     (2006.01)
    *C08L 5/00*     (2006.01)

(56) References Cited

U.S. PATENT DOCUMENTS

2010/0173779 A1     7/2010   Moenne Munoz
2013/0005009 A1*   1/2013   Mody ...................... C12P 7/06
                                                                    435/161

\* cited by examiner

BIOSTIMULANT FORMULATION FOR IMPROVING PLANT GROWTH AND USES THEREOF

RELATED APPLICATIONS

The present patent document is a § 371 national phase application based on International Application Serial No. PCT/IN2016/050133, filed May 9, 2016, designating the United States and published in English, which claims priority to Indian Application Serial No. 2364/CHE/2015, filed May 10, 2015, which are hereby incorporated by reference.

FIELD OF INVENTION

The present disclosure relates to the field of plant biology. The present disclosure provides a biostimulant formulation obtained from juice and juice extracted pulp of at least one seaweed species that is useful in promoting plant growth.

BACKGROUND OF THE INVENTION

Seaweed based biostimulants for improving plant growth has been well known for a long time. Seaweed extracts and suspensions have achieved a broader use and market than seaweed and seaweed meal. The seaweed species used are mostly temperate, which grow in colder waters. Several reviews have covered the use of seaweed extracts for Agriculture (Khan et al. J. Plant Growth Regul. (2009) 28:386-399; Craigie et al—J Appl Phycol (2011) 23:371-393).

Biostimulants are currently mainly made from brown seaweeds, although the species varies between countries. Some are made by alkaline extraction of the seaweed and anything that does not dissolve is removed by filtration (e.g. Maxicrop and Seasol). Others are suspensions of very fine particles of seaweed (Goëmill and Kelpak 66). For Goëmill, the seaweed (*Ascophyllum*) is rinsed, frozen at −25° C., crushed into very fine particles and homogenized; the result is a creamy product with particles of 6-10 micrometers; everything from the seaweed is in the product. Other chemicals may be added to improve the product for particular applications. Kelpak first appeared in 1983 and the originators say it is made from *Ecklonia maxima* by a cell-burst procedure that does not involve the use of heat, chemicals or dehydration. Fresh plants are harvested by cutting from the rocks at the stipe (stalk) and then they are progressively reduced in particle size using wet milling equipment. These small particles are finally passed under extremely high pressure into a low-pressure chamber so that they shear and disintegrate, giving a liquid concentrate. (McHugh, D. 2003. A guide to the seaweed industry Page 92).

U.S. Pat. No. 6,893,479 and its equivalent outlines a process whereby fresh red seaweed *Kappaphycus alvarezii* can be used to produce a biofertilizer by using the juice part of the red seaweed as a growth stimulant. The solids part of the seaweed is dried and converted into carrageenan. This patent does not envisage the use of the solid residue (carrageenan) as a biostimulant.

US 2010/173779 A1, US2011/0099898 A1 and its equivalents outlines a process where the oligo carrageenan polymers of around 20 sulphated galactose units obtained from carrageenan derived from seaweed species have been shown to have growth promoting effects and defense against pathogens.

SUMMARY OF THE INVENTION

In an aspect of the present disclosure, there is provided a biostimulant formulation for improving plant growth comprising a) juice obtained from at least one seaweed species; and b) hydrolysate obtained from at least one seaweed species pulp, wherein the hydrolysate is obtained from the pulp after juice has been extracted from the pulp.

In an aspect of the present disclosure, there is provided a method of preparing a biostimulant formulation comprising a) juice obtained from at least one seaweed species; and b) hydrolysate obtained from at least one seaweed species pulp, wherein the hydrolysate is obtained from the pulp after juice has been extracted from the pulp, said method comprising the steps of: i) obtaining at least one seaweed species; ii) processing said seaweed species to obtain seaweed juice and pulp, wherein the pulp is obtained after extracting juice; iii) subjecting the pulp to hydrolysis to obtain a hydrolysate, said hydrolysis comprising the steps of: (1) diluting the pulp with at least one diluent to obtain suspended solids having weight percentage in the range of 5-15%; (2) adjusting the pH of suspended solids to a range of 1-3.5; (3) adjusting the temperature to a range of 60° C.-140° C. at a rate of 1-5° C. per minute under constant stirring; and (4) holding the temperature for 5-300 minutes to obtain said hydrolysate; iv) concentrating the hydrolysate to a final brix in the range of 17-24 Bx; and v) mixing said juice, and hydrolysate to obtain a biostimulant formulation.

In an aspect of the present disclosure, there is provided a method of treatment of plants for promoting growth, said method comprising the steps of: a) obtaining a biostimulant formulation comprising i) juice obtained from at least one seaweed species; and ii) hydrolysate obtained from at least one seaweed species pulp, wherein the hydrolysate is obtained from the pulp after juice has been extracted from the pulp, and b) contacting said biostimulant formulation with a plant or part thereof, including seeds, wherein said method promotes plant growth.

In an aspect of the present disclosure, there is provided biostimulant formulation comprising a) juice obtained from at least one seaweed species; and b) hydrolysate obtained from at least one seaweed species pulp, wherein the hydrolysate is obtained from the pulp after juice has been extracted from the pulp for hydrolysate obtained from at least one seaweed species pulp, wherein the hydrolysate is obtained from the pulp after juice has been extracted from the pulp.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

BRIEF DESCRIPTION OF THE ACCOMPANYING DRAWINGS

The following drawings form part of the present specification and are included to further illustrate aspects of the present disclosure. The disclosure may be better understood by reference to the drawings in combination with the detailed description of the specific embodiments presented herein.

DETAILED DESCRIPTION OF THE INVENTION

Figure 1:
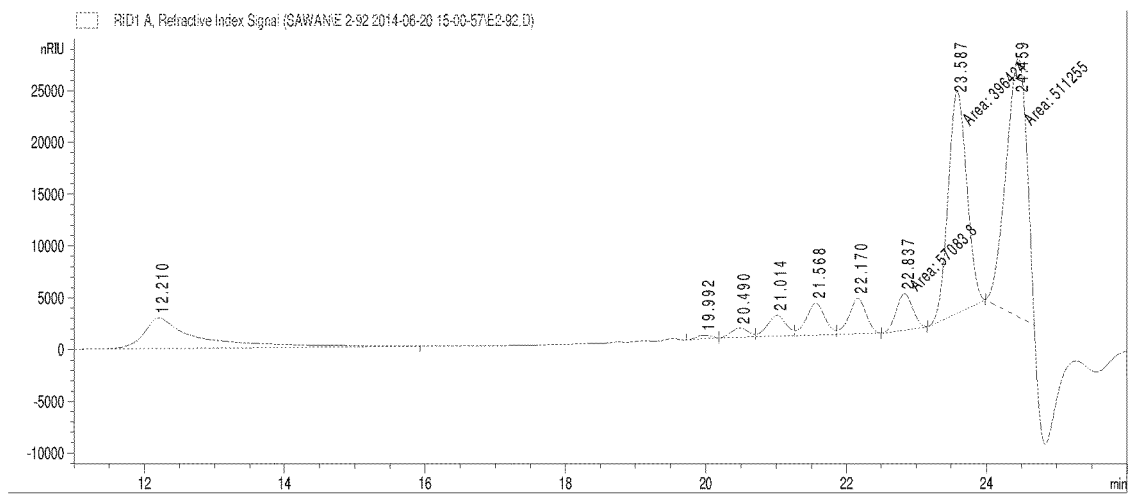
FIG. 1 depicts the chromatogram of hydrolysate obtained from controlled hydrolysis of seaweed juice extracted from *Kappaphycus alvarezii* (cottonii) pulp, in accordance with an embodiment of the present disclosure.

Those skilled in the art will be aware that the present disclosure is subject to variations and modifications other than those specifically described. It is to be understood that the present disclosure includes all such variations and modifications. The disclosure also includes all such steps, features, compositions and compounds referred to or indicated in this specification, individually or collectively, and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

A composition comprising "synergistic activity" or a "synergistic composition" is a combination of compounds which exhibits increased biological or functional activity as a non-linear multiple of the biological or functional activity of the individual compounds. In other words, the combined biological or functional activity of two or more compounds being tested is significantly greater than the expected result based on independent effects of the compounds when tested separately. Synergy may be apparent only at some ranges or concentrations. Also the synergistic combination of the compounds may be different for different kinds of biological effects being tested—for example shoot length increase, root length increase or leaf expansion or yield etc.

The term "juice extracted pulp" refers to seaweed pulp remaining after juice has been extracted from seaweed by any or combination of conventional processes or processes as described in the instant specification.

The present disclosure is not to be limited in scope by the specific embodiments described herein, which are intended for the purposes of exemplification only. Functionally-equivalent products, compositions, and methods are clearly within the scope of the disclosure, as described herein.

In an embodiment of the present disclosure, there is provided a biostimulant formulation for improving plant growth comprising: a) juice obtained from at least one seaweed species; and b hydrolysate obtained from at least one seaweed species pulp, wherein the hydrolysate is obtained from the pulp after juice has been extracted from the pulp.

In an embodiment of the present disclosure, there is provided a biostimulant formulation as described herein, wherein said seaweed species is red seaweed.

In an embodiment of the present disclosure, there is provided a biostimulant formulation as described herein, wherein said seaweed is selected from the group consisting of *Kappaphycus striatus, Eucheuma cottonii, Eucheuma denticulatum (spinosum,) Halymenia durvillaea, Kappaphycus alvarezii, Chondrus crispus, Halymenia durvillei, Porphyra purpurea, Eucheuma denticulatum, Euchuema isifonne, Hypnea musciformis, Solieria filiformis, Mastocarpus stellatus, Porphyra capensis, Gracillaria* sp and combinations thereof.

In an embodiment of the present disclosure, there is provided a biostimulant formulation as described herein, wherein said seaweed is *Halymenia durvillaea*.

In an embodiment of the present disclosure, there is provided a biostimulant formulation as described herein, wherein said seaweed is *Kappaphycus alvarezii*.

In an embodiment of the present disclosure, there is provided a biostimulant formulation as described herein, wherein said seaweed is *Chondrus crispus*.

In an embodiment of the present disclosure, there is provided a biostimulant formulation as described herein, wherein said seaweed is *Halymenia durvillei*.

In an embodiment of the present disclosure, there is provided a biostimulant formulation as described herein, wherein said seaweed is *Porphyra* purpurea.

In an embodiment of the present disclosure, there is provided a biostimulant formulation as described herein, wherein said seaweed is *Eucheuma denticulatum*.

In an embodiment of the present disclosure, there is provided a biostimulant formulation as described herein, wherein said seaweed is *Euchuema isiforme*.

In an embodiment of the present disclosure, there is provided a biostimulant formulation as described herein, wherein said seaweed is *Hypnea musciformis*.

In an embodiment of the present disclosure, there is provided a biostimulant formulation as described herein, wherein said seaweed is *Solieria filiformis*.

In an embodiment of the present disclosure, there is provided a biostimulant formulation as described herein, wherein said seaweed is *Mastocarpus stellatus*.

In an embodiment of the present disclosure, there is provided a biostimulant formulation as described herein, wherein said seaweed is *Porphyra capensis*.

In an embodiment of the present disclosure, there is provided a biostimulant formulation as described herein, wherein said seaweed is *Kappaphycus striatus*.

In an embodiment of the present disclosure, there is provided a biostimulant formulation as described herein, wherein said seaweed is *Eucheuma cottonii*.

In an embodiment of the present disclosure, there is provided a biostimulant formulation as described herein, wherein said seaweed is *Eucheuma spinosum*.

In an embodiment of the present disclosure, there is provided a biostimulant formulation as described herein, wherein said seaweed is a combination of *Eucheuma dendiculatum* and *Kappaphycus striatus*.

In an embodiment of the present disclosure, there is provided a biostimulant formulation as described herein, wherein said seaweed is a combination of seaweeds selected from the group consisting of *Kappaphycus striatus, Eucheuma cottonii, Eucheuma spinosum, Halymenia durvillaea, Kappaphycus alvarezii, Chondrus crispus, Halymenia durvillei, Porphyra purpurea, Eucheuma denticulatum, Euchuema isifonne, Hypnea musciformis, Solieria filiformis, Mastocarpus stellatus*, and *Porphyra capensis, Gracillaria* species In an embodiment of the present disclosure, there is provided a biostimulant formulation as described herein, wherein said juice brix range is from 15-27 Bx.

In an embodiment of the present disclosure, there is provided a biostimulant formulation as described herein, wherein said juice brix range is from 20-27 Bx.

In an embodiment of the present disclosure, there is provided a biostimulant formulation as described herein, wherein said juice brix is 25 Bx.

In an embodiment of the present disclosure there is provided a biostimulant formulation as described herein, wherein in said formulation, the Potassium (K) to Sodium (Na) ion w/w ratio is in the range of 1.5:1 to 15:1.

In an embodiment of the present disclosure there is provided a biostimulant formulation as described herein, wherein in said formulation, the Potassium (K) to Sodium (Na) ion w/w ratio is at least 2:1

In an embodiment of the present disclosure there is provided a biostimulant formulation as described herein, wherein in said formulation, the Potassium (K) to Sodium (Na) ion w/w ratio is 2.7:1.

In an embodiment of the present disclosure there is provided a biostimulant formulation as described herein, wherein in said formulation, the Potassium (K) to Sodium (Na) ion w/w ratio is 4.8:1.

In an embodiment of the present disclosure, there is provided a biostimulant formulation as described herein, wherein said hydrolysate comprises soluble sulphated galacto-oligosachharides having molecular weight ranging from 400-10000 Da.

In an embodiment of the present disclosure, there is provided a biostimulant formulation as described herein, wherein said hydrolysate comprises soluble sulphated galacto-oligosachharides having molecular weight ranging from 400-5000 Da.

In an embodiment of the present disclosure, there is provided a biostimulant formulation as described herein, wherein said hydrolysate comprises soluble sulphated galacto-oligosachharides having degree of polymerization in the range of 2-16.

In an embodiment of the present disclosure, there is provided a biostimulant formulation as described herein, wherein said biostimulant formulation brix is in the range of 10-25 Bx.

In an embodiment of the present disclosure, there is provided a biostimulant formulation as described herein, wherein said biostimulant formulation total carbohydrate concentration is in the range of 5-100 mg/ml.

In an embodiment of the present disclosure, there is provided a biostimulant formulation as described herein, wherein juice to hydrolysate w/w ratio in said formulation is in the range of 1:1-9:1.

In an embodiment of the present disclosure, there is provided a biostimulant formulation as described herein, wherein juice to hydrolysate w/w ratio in said formulation is 4:1.

In an embodiment of the present disclosure, there is provided a biostimulant formulation as described herein, further comprising suitable carriers, diluents, and excipients.

In an embodiment of the present disclosure, there is provided a biostimulant formulation as described herein, wherein said suitable carriers, diluents, and excipients, can be, but not limited to salts such as potassium chloride, potassium sulphate, potassium citrate, sodium sulphate, sodium metabisulfite, sodium citrate, calcium carbonate, calcium phosphate, maltodextrin, gypsum, bentonite, water, sugar, sodium benzoate, potassium sorbate, ethanol, butanol, isopropyl alcohol, acetic acid, lactic acid, and combinations thereof.

In an embodiment of the present disclosure, there is provided a biostimulant formulation as described herein, wherein said formulation is in the form of a liquid.

In an embodiment of the present disclosure, there is provided a biostimulant formulation as described herein, wherein said formulation is in powder form.

In an embodiment of the present disclosure, there is provided a method of preparing a biostimulant formulation as described herein, said method comprising the steps of: a) obtaining at least one seaweed species; b) processing said seaweed species to obtain seaweed juice and pulp, wherein the pulp is obtained after extracting juice; c) subjecting the pulp to hydrolysis to obtain a hydrolysate, said hydrolysis comprising the steps of: (i) diluting the pulp with at least one diluent to obtain suspended solids having weight percentage in the range of 5-15%; (ii) adjusting the pH of suspended solids to a range of 1-3.5; (iii) adjusting the temperature to a range of 60° C.-140° C. at a rate of 1-5° C. per minute under constant stirring; and (iv) holding the temperature for 5-300 minutes to obtain said hydrolysate; d) concentrating the hydrolysate to a final brix in the range of 17-24 Bx; and e) mixing said juice, and hydrolysate to obtain a biostimulant formulation.

In an embodiment of the present disclosure, there is provided a method of preparing a biostimulant formulation as described herein, wherein said species of seaweed is red seaweed.

In an embodiment of the present disclosure, there is provided a method of preparing a biostimulant formulation as described herein, wherein said species of seaweed is selected from the group consisting of *Kappaphycus striatus, Eucheuma cottonii, Eucheuma spinosum, Halymenia durvillaea, Kappaphycus alvarezii, Chondrus crispus, Halymenia durvillei, Porphyra purpurea, Eucheuma denticulatum,*

*Euchuema isiforme, Hypnea musciformis, Solieria filiformis, Mastocarpus stellatus, Porphyra capensis*, and combinations thereof.

In an embodiment of the present disclosure, there is provided a method of preparing a biostimulant formulation as described herein, wherein said species of seaweed is *Kappaphycus striatus*.

In an embodiment of the present disclosure, there is provided a method of preparing a biostimulant formulation as described herein, wherein species of seaweed is *Eucheuma cottonii*.

In an embodiment of the present disclosure, there is provided a method of preparing a biostimulant formulation as described herein, wherein said species of seaweed is *Eucheuma spinosum*.

In an embodiment of the present disclosure, there is provided a method of preparing a biostimulant formulation as described herein, wherein said seaweed is *Halymenia durvillaea*.

In an embodiment of the present disclosure, there is provided a method of preparing a biostimulant formulation as described herein, wherein said seaweed is *Kappaphycus alvarezii*.

In an embodiment of the present disclosure, there is provided a method of preparing a biostimulant formulation as described herein, wherein said seaweed is *Chondrus crispus*.

In an embodiment of the present disclosure, there is provided method of preparing a biostimulant formulation as described herein, wherein said seaweed is *Halymenia durvillei*.

In an embodiment of the present disclosure, there is provided a method of preparing a biostimulant formulation as described herein, wherein said seaweed is *Porphyra purpurea*.

In an embodiment of the present disclosure, there is provided a method of preparing a biostimulant formulation as described herein, wherein said seaweed is *Eucheuma denticulatum*.

In an embodiment of the present disclosure, there is provided a method of preparing a biostimulant formulation as described herein, wherein said seaweed is *Euchuema isiforme*.

In an embodiment of the present disclosure, there is provided a method of preparing a biostimulant formulation as described herein, wherein said seaweed is *Hypnea musciformis*.

In an embodiment of the present disclosure, there is provided a method of preparing a biostimulant formulation as described herein, wherein said seaweed is *Solieria filiformis*.

In an embodiment of the present disclosure, there is provided a method of preparing a biostimulant formulation as described herein, wherein said seaweed is *Mastocarpus stellatus*.

In an embodiment of the present disclosure, there is provided a method of preparing a biostimulant formulation as described herein, wherein said seaweed is *Porphyra capensis*.

In an embodiment of the present disclosure, there is provided a method of preparing a biostimulant formulation as described herein, wherein said seaweed is a combination of *Eucheuma dendiculatum* and *Kappaphycus striatus*.

In an embodiment of the present disclosure, there is provided a method of preparing a biostimulant formulation as described herein, wherein juice concentration is in the range of 15-27 Bx.

In an embodiment of the present disclosure, there is provided a method of preparing a biostimulant formulation as described herein, wherein juice concentration is in the range of 20-27 Bx.

In an embodiment of the present disclosure, there is provided a method of preparing a biostimulant formulation as described herein, wherein concentration of juice is 25 Bx.

In an embodiment of the present disclosure, there is provided a method of preparing a biostimulant formulation as described herein, wherein s suspended solids concentration is in the range of 5-15%.

In an embodiment of the present disclosure, there is provided a method of preparing a biostimulant formulation as described herein, wherein suspended solids concentration is 10%.

In an embodiment of the present disclosure, there is provided a method of preparing a biostimulant formulation as described herein, wherein pH of suspended solids pH is less than 4.

In an embodiment of the present disclosure, there is provided a method of preparing a biostimulant formulation as described herein, wherein suspended solids pH is less than 3.

In an embodiment of the present disclosure, there is provided a method of preparing a biostimulant formulation as described herein, wherein pH of suspended solids pH is in the range of 1.5-2.

In an embodiment of the present disclosure, there is provided a method of preparing a biostimulant formulation as described herein, wherein the holding temperature of suspended solids is in the range of 90° C.-95° C.

In an embodiment of the present disclosure, there is provided a method of preparing a biostimulant formulation as described herein, wherein the holding temperature of suspended solids is 140° C.

In an embodiment of the present disclosure, there is provided a method of preparing a biostimulant formulation as described herein, wherein the holding temperature of suspended solids is 60° C.

In an embodiment of the present disclosure, there is provided a method of preparing a biostimulant formulation as described herein, wherein temperature of suspended solids is raised to holding temperature at the rate of 1-5° C./minute.

In an embodiment of the present disclosure, there is provided a method of preparing a biostimulant formulation as described herein, wherein initial temperature of suspended solids is in the range of 20-25° C.

In an embodiment of the present disclosure, there is provided a method of preparing a biostimulant formulation as described herein, wherein the suspended solids at 120° C. is held for 20 minutes at a pH of 2.8

In an embodiment of the present disclosure, there is provided a method of preparing a biostimulant formulation as described herein, wherein the suspended solids at 90-95° C. is held for 120 minutes at a pH of 3.2

In an embodiment of the present disclosure, there is provided a method of preparing a biostimulant formulation as described herein, wherein the suspended solids at 60° C. is held for 180 minutes at a pH less than 3.5

In an embodiment of the present disclosure, there is provided a method of preparing a biostimulant formulation as described herein, wherein said at least one diluent is selected from the group consisting of soft water, hard water, sea water, and combinations thereof In an embodiment of the present disclosure, there is provided a method of preparing a biostimulant formulation as described herein, wherein said at least one diluent is soft water.

In an embodiment of the present disclosure, there is provided a method of preparing a biostimulant formulation as described herein, wherein said at least one diluent is hard water.

In an embodiment of the present disclosure, there is provided a method of preparing a biostimulant formulation as described herein, wherein said at least one diluent is sea water.

In an embodiment of the present disclosure, there is provided a method of preparing a biostimulant formulation as described herein, wherein said at least one diluent is a mixture of soft water, hard water, and sea water.

In an embodiment of the present disclosure, there is provided a method of preparing a biostimulant formulation as described herein, wherein said hydrolysate comprises soluble sulphated galacto-oligosachharides having molecular weight ranging from 400-10000 Da.

In an embodiment of the present disclosure, there is provided a method of preparing a biostimulant formulation as described herein, wherein said hydrolysate comprises soluble sulphated galacto-oligosachharides having molecular weight ranging from 400-5000 Da.

In an embodiment of the present disclosure, there is provided a method of preparing a biostimulant formulation as described herein, wherein said hydrolysate comprises soluble sulphated galacto-oligosachharides having degree of polymerization in the range of 2-16.

In an embodiment of the present disclosure, there is provided a method of preparing a biostimulant formulation as described herein, wherein juice to hydrolysate w/w ratio is in the range of 1:9-15:1

In an embodiment of the present disclosure, there is provided a method of preparing a biostimulant formulation as described herein, wherein juice to hydrolysate w/w ratio 4:1.

In an embodiment of the present disclosure, there is provided a method of preparing a biostimulant formulation as described herein, wherein said biostimulant formulation further comprises suitable carriers, diluents, and excipients.

In an embodiment of the present disclosure, there is provided a method of treatment of plants for promoting growth, said method comprising: (a) obtaining a biostimulant formulation as described herein; and (b) contacting said biostimulant formulation with a plant or parts thereof, including seeds, wherein said method promotes plant growth.

In an embodiment of the present disclosure, there is provided a method of treatment of plants for promoting growth, wherein said method increases yield.

In an embodiment of the present disclosure, there is provided a method of treatment of plants for promoting growth, wherein said method increases root length.

In an embodiment of the present disclosure, there is provided a method of treatment of plants for promoting growth, wherein said method increases shoot length.

In an embodiment of the present disclosure, there is provided a method of treatment of plants for promoting growth, wherein said method increases leaf area.

In an embodiment of the present disclosure, there is provided a method of treatment of plants for promoting growth, wherein said method hastens plant maturation.

In an embodiment of the present disclosure, there is provided a biostimulant formulation as described herein for use in promoting plant growth, said plant growth can be increased yield, increased root length, increased leaf area, increased shoot growth, early maturation, and combinations thereof.

Although the subject matter has been described in considerable detail with reference to certain preferred embodiments thereof, other embodiments are possible.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein. It is to be understood that this disclosure is not limited to particular methods, and experimental conditions described, as such methods and conditions may vary.

Example 1

Separation of *Kappaphycus striatus* (Sacol) Seaweed into Juice and Juice Extracted Pulp 1 kg of fresh *Kappaphycus striatus* (sacol) seaweed was sourced from Makassar Island in Indonesia and processed through a lab centrifugal juicer. The centrifugal juicer is equipped with a rotating perforated bowl with sharp teeth. Whole seaweed comes into contact with the rotating bowl and is immediately separated into juice and juice extracted pulp without forming intermediate slurry. The seaweed juice extracted pulp and the seaweed juice were collected separately in a continuous manner from two different outlets of the equipment. The amount of juice extracted pulp collected was 350 g and the amount of juice collected was 650 g. The moisture content of the juice extracted pulp was 80% and the Brix of the juice was 5%.

Example 2

Separation of *Spinosum* Seaweed into Juice and Juice Extracted Pulp 1 kg of *Eucheuma dendiculatum* (*Spinosum*) was obtained from Zanzibar Island in Tanzania packed in a transparent plastic bag and exposed to sun for 4-10 h. The juice leached out of biomass was collected in a bag, leaving intact whole seaweed behind and without forming any slurry. From 1 kg of fresh *spinosum,* 800 g of juice extracted pulp and 200 gm of juice was obtained.

Example 3

Concentration of Seaweed Juice (SWJ)

150 ml of fresh *Spinosum* seaweed juice from Example 2 (approx 4.5 Bx) was concentrated using rotary evaporator maintained under a vacuum of 680 mm of Hg to approximately 30 ml. The evaporating flask was maintained at 65° C. and the vertical condenser was maintained at 4° C. by circulating water through the chiller. The Brix of the final concentrated juice was 22 Bx. In another similar experiment 1 kg of *Kappapycus Alvarezii* (cottonii) seaweed was separated into juice and pulp my methods in Example 1. 250 ml of juice (approx. 5 Bx) was concentrated in a rotarty vacuum evaporator to a final Bx of 25.

The concentrated juices of both *spinosum* and cottonii were sent for elemental analysis which showed the following composition as shown below in Table 1(g/Kg).

TABLE 1

| | Seaweed variety | | | |
|---|---|---|---|---|
| | Spinosum | | Cottonii | |
| Element | Conc g/kg | Ratio K/Element | Conc g/kg | Ratio K/Element |
| Potassium(K) | 36.00 | 1 | 37.5 | 1 |
| Sodium | 13.10 | 2.7 | 7.8 | 4.8 |
| Calcium | 1.90 | 18.9 | 2.0 | 18.6 |
| Magnesium | 3.00 | 12 | 1.6 | 23.4 |
| Phosphorous | 0.34 | 105.9 | 0.18 | 208.3 |
| Sulphur | 4.0 | 9 | 7.5 | 5 |
| Iron | 0.02 | 1800 | 0.01 | 3750 |

It can be seen from the above analysis that irrespective of the seaweed species, potassium is the most abundant element present in the concentrated juice. It can also be seen that the ratio of potassium is more than 2 times that of the next most abundant element, sodium.

Example 4

Stability of the Juice Concentrate

Both single strength juice (5 Bx) and concentrated juice (25 Bx) from Example 3 were aliquoted in to 100 ml of screw capped Erlenmeyer flask. The flasks were incubated at 25° C. on a rotary shaker set at 100 rpm. After one week of incubation, it was observed that the single strength juice had a foul smell emanating indicating its spoilage due to microbial contamination. However, the concentrated juice did not have any foul smell, indicating that it was stable.

Example 5

Controlled Hydrolysis of Juice Extracted Pulp 1 kg of fresh *Kappaphycus alvarezii* (cottonii) obtained from Makassar island in Indonesia was processed as described in Example 1. The pulp obtained after juice extraction was mixed with water to obtain suspended solids having concentration of 10%. The pH of the seaweed pulp was brought down using acid to 2.5, and the temperature was gradually raised to about 121° C. using an autoclave in a step-wise manner. The mixture was held between 120-122° C. for about 15 minutes under constant stirring conditions. The hydrolysis was stopped by cooling the reaction mixture. A sample was injected into the HPLC and a ladder like pattern of oligosaccharides was obtained as shown in FIG. 1.

Figure 6:
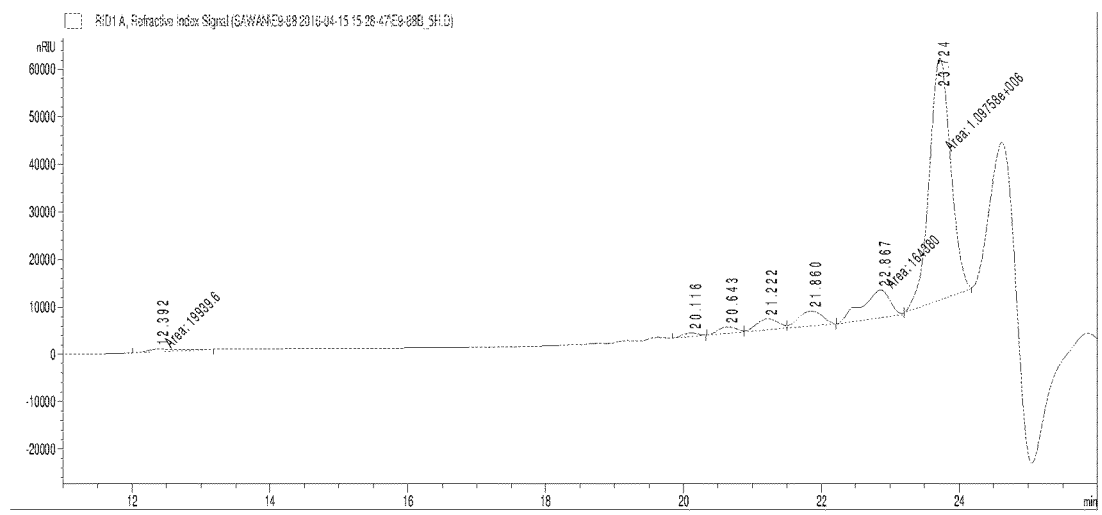
FIG. 6 depicts the chromatogram of hydrolysate obtained from controlled hydrolysis of juice extracted from *Eucheuma dendiculatum* (*spinosum*) pulp, in accordance with an embodiment of the present disclosure

In another experiment, a 10% dry solids equivalent suspension of pulp (after juice extraction) of *Eucheuma dendiculatum* (*spinosum*) obtained as outlined in example 2 was prepared. The pH of the suspension was lowered using 0.05 M HCL to 3.5 and the suspension was gradually heated to 93° C. and held for 5 h between 90 and 95° C. Samples of the mixture were taken at regular time intervals and assayed using a HPLC system. The hydrolysis was stooped by cooling the reaction mixture. A ladder like pattern of oligosaccharides was detected as shown in FIG. 6.

Example 6

Analytical Procedure to Check the Seaweed Pulp (Juice Extracted) Hydrolysate

The samples obtained from the hydrolysis process as described above in Example 5 were centrifuged and the supernatant was analyzed using an HPLC system (Infinity 1200, Agilent Technologies) equipped with a gel filtration column (TSKgel G2000SWXL, Tosho Bioscience) and a refractive index detector. The mobile phase, 0.2 M Ammonium acetate (pH 5.0) was used at a flow rate of 0.5 ml/min. A ladder like pattern of oligosaccharides was obtained as shown in FIG. 1. This pattern corresponds to series of peaks at regular intervals from 19 minutes to 24 minutes under the conditions of the HPLC analysis. The peaks represent increasing chain length of oligosaccharides ranging from a high to low degree of polymerization.

For determination of molecular weight of oligosaccharides, the column was calibrated with Dextran GPC standards (Sigma, Cat no. 31416, 31417 and 31418). The accuracy of the standard curve was tested using sulphated oligosaccharides (Neocarrabiose-4-O-sulfate sodium salt; Neocarratetraose-41, 43-di-O-sulfate sodium salt, obtained from Dextra UK) of known molecular weight. The molecular weight derived using standard curve was accurate to about ±15%. It was seen that all the significant peaks in the chromatogram occur after 20 minutes which indicates that the molecular weight is less than 8,500 Da.

Example 7

Concentration of Seaweed Juice Extracted Pulp Hydrolysate (SWO)

300 ml of oligosaccharide containing hydrolysate obtained from Experiment 5 (typically 7 Bx) was concentrated using rotary evaporator maintained under a vacuum of 680 mm of Hg to approximately 100 ml. The evaporating flask was maintained at 65° C. and the vertical condenser was maintained at 4° C. by circulating water through the chiller. The Brix of the concentrated hydrolysate was 21 Bx.

Example 8

Maize Seedling Root Length Bio-Assay

Maize seedlings were treated with a mixture of concentrated seaweed juice (SWJ) and concentrated juice extracted seaweed pulp hydrolysate (SWO) at a w/w ratio of 4:1 (juice concentration of 0.8 ml/L, and hydrolysate concentration of 0.2 ml/L), or individually with concentrated seaweed juice (0.8 ml/L) or concentrated juice extracted seaweed pulp hydrolysate (0.8 ml/L). Water was used as control. The results are given below in Table 2 in tabulated format, and in graph format in FIG. 2.

TABLE 2

| | | | Concentration (ml/L) | |
|---|---|---|---|---|
| Treatment | w/w ratio | Root length (cm) | SWJ | SWO |
| Control | — | 18.45 ± 3.18 (0%) | 0 | 0 |
| SWJ:SWO | 4:1 | 25.5 ± 3.06 (38.21%) | 0.8 | 0.2 |
| SWJ | — | 19 ± 4.74 (2.98%) | 0.8 | 0 |
| SWO | — | 22.4 ± 3.34 (21.41%) | 0 | 0.8 |

Figure 2:
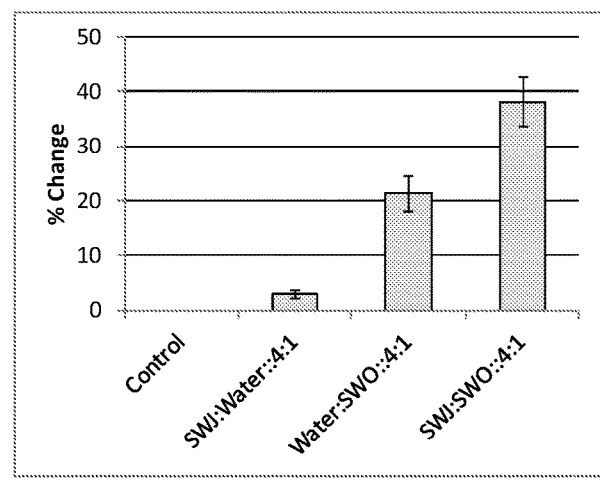
FIG. 2 depicts the graphical representation of the effect of a biostimulant formulation as described herein on maize seedling root length, in accordance with an embodiment of the present disclosure.

As observed from FIG. 2, and Table 2, increase in mean root length over control was much significantly more when SWJ and SWO were used in a mixture (38.21%) compared to the effect of SWJ or SWO alone. SWJ alone gave a 2.98% increase over control while SWO gave a 21.41% increase over control. The additive effect of both these components theoretically would have been 24.39%, which is much less than the effect obtained when both are used together as observed, thus signifying a surprising and unexpected synergistic effect.

Example 9

Horse Gram Seed Shoot Length Bio-assay

Horse gram seeds were treated with a mixture of concentrated seaweed juice (SWJ) and concentrated juice extracted seaweed pulp hydrolysate (SWO) at a w/w ratio of 4:1 (juice concentration of 0.8 ml/L, and hydrolysate concentration of 0.2 ml/L), or individually with concentrated seaweed juice (0.8 ml/L) or concentrated juice extracted seaweed pulp hydrolysate (0.8 ml/L). Water was used as control. The results are given below in Table 3 in tabulated format, and in graph format in FIG. 3.

TABLE 3

| Treatment | w/w ratio | shoot length (cm) | Concentration (ml/L) SWJ | SWO |
|---|---|---|---|---|
| Control | — | 6.71 ± 0.86 (0%) | 0 | 0 |
| SWJ:SWO | 4:1 | 7.32 ± 0.95 (9.13%) | 0.8 | 0.2 |
| SWJ | — | 6.68 ± 1.06 (−0.45%) | 0.8 | 0 |
| SWO | — | 6.93 ± 1.54 (3.34%) | 0 | 0.8 |

Figure 3:
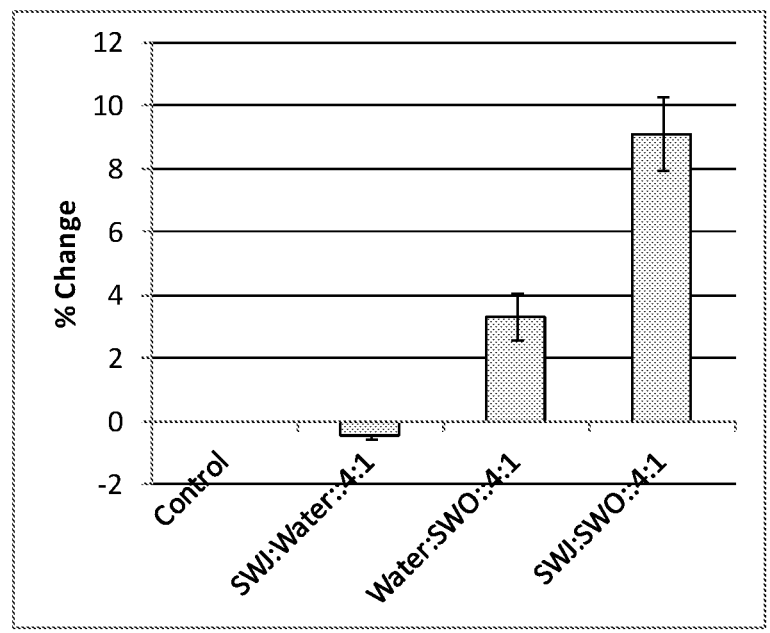
FIG. 3 depicts the graphical representation of the effect of a biostimulant formulation as described herein on horse gram seed shoot length, in accordance with an embodiment of the present disclosure.

As observed from FIG. 3, and Table 3, increase in mean shoot length over control was much significantly more when SWJ and SWO were used in a mixture (9.13%) compared to the effect of SWJ or SWO alone. SWJ alone gave a negative 0.45% increase over control while SWO gave a 3.34% increase over control. The additive effect of both these components theoretically would have been 2.89%, which is much less than the effect obtained when both are used together as observed, thus signifying a surprising and unexpected synergistic effect.

Example 10

Cucumber Cotyledon Expansion Bio-assay

Cucumber cotyledons were treated with a mixture of concentrated seaweed juice (SWJ) and concentrated juice extracted seaweed pulp hydrolysate (SWO) at a w/w ratio of 4:1 (juice concentration of 0.8 ml/L, and hydrolysate concentration of 0.2 ml/L), or individually with concentrated seaweed juice (0.8 ml/L) or concentrated juice extracted seaweed pulp hydrolysate (0.8 ml/L). Water was used as control. The results are given below in Table 4 in tabulated format, and in graph format in FIG. 4.

TABLE 4

| Treatment | w/w ratio | Cotyledon expansion (cm²) | Concentration (ml/L) SWJ | SWO |
|---|---|---|---|---|
| Control | — | 0.83 ± 0.14 (0%) | 0 | 0 |
| SWJ:SWO | 4:1 | 1.58 ± 0.23 (90.36%) | 0.8 | 0.2 |
| SWJ | — | 0.96 ± 0.07 (15.66%) | 0.8 | 0 |
| SWO | — | 1.26 ± 0.10 (51.81%) | 0 | 0.8 |

Figure 4:
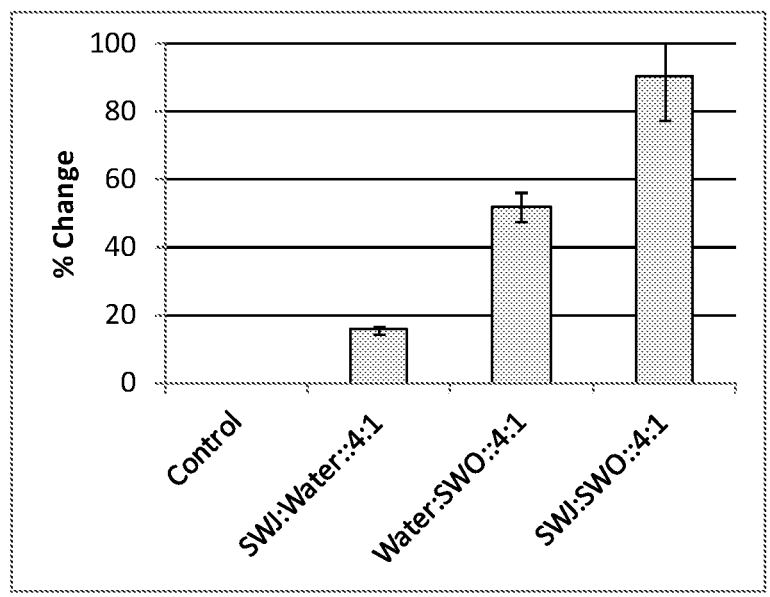
FIG. 4 depicts the graphical representation of the effect of a biostimulant formulation as described herein on cucumber cotyledon expansion, in accordance with an embodiment of the present disclosure.

As observed from FIG. 4, and Table 4, increase in mean cotyledon over control was much significantly more when SWJ and SWO were used in a mixture (90.36%) compared to the effect of SWJ or SWO alone. SWJ alone gave a 15.66% increase over control while SWO gave a 51.81% increase over control. The additive effect of both these components theoretically would have been 67.47%, which is much less than the effect obtained when both are used together as observed, thus signifying a surprising and unexpected synergistic effect.

Example 11

Spray Drying to Obtain Powder Biostimulant Product

Concentrated juice from *Eucheuma cottonii* from Indonesia (with a Brix of 23) was converted into powder form using FT-80 Tall form spray dryer at the following conditions: Inlet temperature 174° C. and outlet temperature 84° C.

Biostimulant formulations were prepared by blending SWJ and SWO in the appropriate weight ratios (1:1-9:1) and spray drying would be carried out at the similar conditions mentioned above to obtain the solid biostimulant formulations.

Example 12

Horse Gram Germination Root Length Bio-assay

Horse gram seeds were treated with a mixture of concentrated seaweed juice (SWJ) and concentrated juice extracted seaweed pulp hydrolysate (SWO) at a w/w ratio of 12:1 (juice concentration of 4.0 ml/L, and hydrolysate concentration of 0.33 ml/L), or individually with concentrated seaweed juice (4.0 ml/L) or concentrated juice extracted seaweed pulp hydrolysate (0.33 ml/L). Water was used as control. The results are given below in Table 5 in tabulated format, and in graph format in FIG. 5.

TABLE 5

| Treatment | w/w ratio | Root length (cm) | Concentration (ml/L) SWJ | SWO |
|---|---|---|---|---|
| Control | — | 11.06 ± 1.25 (0%) | 0 | 0 |
| SWJ:SWO | 12:1 | 12.88 ± 1.37 (16.4%) | 4.0 | 0.33 |
| SWJ | — | 11.26 ± 1.54 (1.8%) | 4.0 | 0 |
| SWO | — | 12.43 ± 1.60 (12.4%) | 0 | 0.33 |

Figure 5:
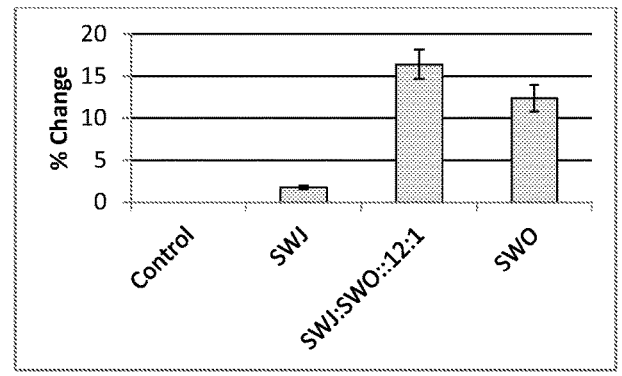
FIG. 5 depicts the graphical representation of the effect of a biostimulant formulation as described herein on maize seeding shoot length, in accordance with an embodiment of the present disclosure.

As observed from FIG. 5, and Table 5, increase in mean shoot length over control was much more when SWJ and SWO were used in a mixture (16.4%) compared to the effect of SWJ or SWO alone. SWJ alone gave a 1.8% increase over control while SWO gave a 12.4% increase over control. The additive effect of both these components theoretically would have been 14.2%, which is much less than the effect obtained when both are used together as observed, thus signifying a surprising and unexpected synergistic effect.

Example 13

Rice Field Trial Yield Results

A field trial was carried out with SWJ and SWO and mixtures of SWJ and SWO in various proportions. Rice seeds were germinated in a nursery for 21 days and the grown seedlings were transplanted into prepared fields plots and sprayed with the Biostimulants at intervals of 30 days and 60 days after transplantation. The results typically obtained are given below in table 6.

TABLE 6

| Treatment | w/w ratio | Grain yield Quintals/acre | Concentration (ml/L) SWJ | SWO |
|---|---|---|---|---|
| Control | — | 17.71 (0%) | 0 | 0 |
| SWJ:SWO | 2:1 | 23.71 (33.9%) | 10 | 5 |
| SWJ | — | 18.83 (6.3%) | 10 | 0 |
| SWO | — | 20.91 (18.1%) | 0 | 5 |

These results again serve to demonstrate the surprising synergy that is obtained in the biostimulant effect by using the Seaweed juice (SWJ) and the Seaweed Oligosaccharides (SWO) simultaneously instead of separately. The SWJ alone gives an increase of about 6.3% yield increase over control. The SWO alone gives about 18.1% yield increase over control. The expected additive effect should have been 24.1% but surprisingly, an increase of 33.9% was obtained.

Example 14

Mixing SWJ of One Species with SWO of Another Species.

The juice from *Kappaphycus striatus* (saccol) from example 1 was concentrated following the method in example 3 to obtain a seaweed juice concentrate (SWJ). Simultaneously, the oligosaccharide containing hydrolysate obtained by controlled hydrolysis of the juice extracted pulp from *Eucheuma dendiculatum* (spinsoum) as explained in Example 5 was concentrated as explained in example 7 to obtain a concentrated hydrolysate (SWO). The SWJ and the SWO were blended in a proportion of 1:1 to obtain a Biostimulant product. The individual SWJ and the SWO as well as the blend were both tested in a pot trial using tomato plants as a test crop. It was once again found that the yield obtained by using blend made from saccol SWJ and *spinosum* SWO was significantly better than the to the performance of the individual components, once again demonstrating the synergistic effect obtained by blending the SWJ and SWO.

Overall, the present disclosure provides a biostimulant formulation obtained from at least one species of seaweed that surprisingly and unexpectedly shows a synergistic effect in promoting plant growth when applied to plant or parts thereof including seeds. The observed synergism is in part due to the composition of the said formulation, which comprises of seaweed juice and juice extracted seaweed pulp hydrolysate mixed at particular w/w ratios. The unexpected synergism is not seen upon treatment with juice or hydrolysate alone, nor a combination is reported previously in prior art.

We claim:

1. A biostimulant formulation for improving plant growth comprising:
   a. juice obtained from at least one seaweed species; and
   b. hydrolysate obtained from at least one seaweed species pulp,
   wherein the hydrolysate is obtained from the pulp after juice has been extracted from the pulp: and
   wherein the hydrolysate comprises soluble sulphated galacto-oligosaccharides having molecular weight in a range of 400-10000 Da.

2. The biostimulant formulation of claim 1, wherein said seaweed species is a red seaweed.

3. The biostimulant formulation of claim 2, wherein said red seaweed is selected from the group consisting of *Kappaphycus striatus, Eucheuma cottonii, Eucheuma spinosum, Halymenia durvillaea, Kappaphycus alvarezii, Chondrus crispus, Halymenia durvillei, Porphyra purpurea, Eucheuma denticulatum, Euchuema isiforme, Hypnea musciformis, Solieria filiformis, Mastocarpus stellatus, Porphyra capensis,* and combinations thereof.

4. The biostimulant of claim 3, wherein said red seaweed is *Kappaphycus alvarezii*.

5. The biostimulant of claim 3, wherein said red seaweed is *Eucheuma dendiculatum*.

6. The biostimulant of claim 3, wherein red seaweed is a combination of *Eucheuma dendiculatum* and *Kappaphycus striatus*.

7. The biostimulant formulation of claim 1, wherein said juice has a brix in a range of 15-27 Bx.

8. The biostimulant formulation of claim 1, wherein the soluble galacto-oligosaccharides have degree of polymerization in the range of 2-16.

9. The biostimulant formulation of claim 1, wherein said biostimulant formulation has a brix in the range of 10-25 Bx.

10. The biostimulant formulation of claim 1, wherein said biostimulant formulation has a carbohydrate concentration in the range of 5-100 mg/ml.

11. The biostimulant formulation of claim 1, wherein juice to hydrolysate w/w ratio in said formulation is in the range of 1:9-15:1.

12. The biostimulant formulation of claim 1, further comprising carriers, diluents, and excipients.

13. The biostimulant formulation of claim 1 for use in promoting plant growth, said plant growth being measured in terms of at least one member selected from the group consisting of an increased yield, increased root length, increased leaf area, increased shoot growth, early maturation, and combinations thereof.

14. A method of preparing the biostimulant formulation of claim 1, said method comprising the steps of:
   a. obtaining at least one seaweed species;
   b. processing said seaweed species to obtain seaweed juice and pulp, wherein the pulp is obtained after extracting juice;
   c. subjecting the pulp to hydrolysis to obtain a hydrolysate, said hydrolysis comprising the steps of:
      i. diluting the pulp with at least one diluent to obtain suspended solids having weight percentage in the range of 5-15%;
      ii. adjusting the pH of suspended solids to a range of 1-3.5;
      iii. adjusting the temperature to a range of 60° C.-140° C. at a rate of 1-5° C. per minute under constant stirring; and
      iv. holding the temperature for 5-300 minutes to obtain said hydrolysate;
   d. concentrating the hydrolysate to a final brix in the range of 17-24 Bx; and
   e. mixing said juice and hydrolysate to obtain the biostimulant formulation.

15. The method of claim 14, said method further comprising contacting carriers, diluents, and excipients with said biostimulant formulation.

16. The method of claim 15, wherein said diluent is selected from the group consisting of hard water, soft water, sea water, and combinations thereof.

17. A method of treatment of plants to promote plant growth, said method comprising the steps of:
   a. obtaining the biostimulant formulation of claim 1; and
   b. contacting said biostimulant formulation with a plant or a part thereof, including seeds,
   wherein said method promotes plant growth.

18. The method of claim 17, wherein plant growth is measured in terms of at least one member seleted from the group consisting of an increased yield, increased root length, increased leaf area, increased shoot growth, early maturation, and combinations thereof.

* * * * *